United States Patent [19]

Mülhaupt et al.

[11] Patent Number: 4,963,636
[45] Date of Patent: Oct. 16, 1990

[54] ADHESION PROMOTERS

[75] Inventors: Rolf Mülhaupt, Marly, Switzerland; Hubert Simon, Mulhouse, France

[73] Assignee: Ciba-Geigy Corporation, Ardsley, N.Y.

[21] Appl. No.: 479,223

[22] Filed: Feb. 12, 1990

Related U.S. Application Data

[63] Continuation of Ser. No. 220,339, Jul. 14, 1988, abandoned, which is a continuation of Ser. No. 118,817, Nov. 9, 1987, abandoned.

[30] Foreign Application Priority Data

Nov. 19, 1986 [CH] Switzerland .............. 4618/86

[51] Int. Cl.$^5$ ............................................. C08G 77/04
[52] U.S. Cl. ........................................ 528/28; 528/29; 528/30; 528/44; 528/59; 528/60; 528/76; 528/80; 528/85; 528/901; 528/903
[58] Field of Search ................... 528/28, 29, 30, 44, 528/59, 60, 76, 80, 85, 901, 903

[56] References Cited

U.S. PATENT DOCUMENTS

| | | | |
|---|---|---|---|
| 3,632,557 | 1/1972 | Brode et al. | 528/59 |
| 4,491,650 | 1/1985 | Rizk et al. | 525/102 |
| 4,539,345 | 9/1985 | Hansen | 524/114 |
| 4,625,012 | 11/1986 | Rizk et al. | 528/29 |

FOREIGN PATENT DOCUMENTS 3414877 10/1985 Fed. Rep. of Germany .

OTHER PUBLICATIONS

H. Ono et al., J. Poly. Sci., Poly Letters Ed. 23, 509 (1985).

Primary Examiner—John Kight, III
Assistant Examiner—Sam A. Acquati
Attorney, Agent, or Firm—Stephen V. O'Brien

[57] ABSTRACT

Compounds of formula (I)

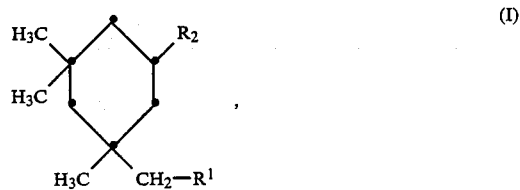

wherein one of the radicals $R^1$ or $R^2$ is $-N=C=O$ and the other is $-NHC(O)S(CH_2)_3Si(OR^3)_3$, wherein $R^3$ is $C_1-C_4$ alkyl or phenyl, are most suitable for use as adhesion promoters for polyurethane single-component or two-component adhesives and also as primers.

1 Claim, No Drawings

ADHESION PROMOTERS

This application is a continuation of application Ser. No. 220,339, filed July 14, 1988, now abandoned, which is a continuation of Ser. No. 118,817, filed Nov. 9, 1987, now abandoned.

The present invention relates to silicon modified isophorone isocyanates, to a process for their manufacture, to the use thereof as adhesion promoters, as well as to polyurethanes containing such compounds.

Polyurethanes are customarily used as adhesives, sealing compounds, paints or insulating materials. Prepolymers having isocyanate end groups may be reacted, i.e. cured, either with amine compounds or hydroxy compounds as well as with water. Curing with water is preferably effected for single-component systems, utilising atmospheric moisture and also the water skin on the substrates to be bonded as hardener for the prepolymer.

To improve the adhesive properties of adhesive layers on the surfaces of substrates to be bonded, surface pretreatments in the form of mechanical and/or chemical processes are carried out which serve the purpose of either making possible or promoting the formation of physical and chemical intermolecular forces. These pretreatments, which also include the application of so-called primers, are complemented by the use of adhesion promoters based on organosilicon compounds (silanes). These adhesion promoters are either applied to the surfaces of the substrates to be bonded or added to the adhesive. They are able to enhance the strength of adhesive bonds and, in particular, their resistance to ageing caused by humid atmospheres. Such adhesion promoters have, for example, long been used in the manufacture of glass fibre-reinforced plastics to improve the adhesion between glass fibres and the appropriate matrix resin (coherent, continuous phase of a multi-phase polymer). The function of adhesion promoters is thus to complement the effect of conventional chemical surface treatments or even—especially in combination with mechanical processes—in some cases to replace them.

In the field of adhesives, use is made, for example, of silane adhesion promoters having the general formula

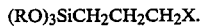

Customary R substituents are $C_1$-$C_4$ alkyl groups. The reactive end group X, in conformity with the adhesive layer polymer, may for example be an amino, hydroxy, vinyl, methacrylate or epoxy group.

The surface treatment of the substrates to be bonded creates surface conditions which shall provide the prerequisites for optimum adhesive properties of the adhesive layers. For this reason it is necessary either to effect bonding of the pretreated substrates to be bonded either immediately afterwards or after as short an interval of time as possible, so as to avoid renewed deactivation of the surface. Situations may, however, arise in which the surface pretreatment is conveniently carried out by the manufacturer of the material in a continuous manufacturing process and bonding is effected separately by the user or in other sectors of the plant, in which case there will be substantial lapses of time between surface treatment and processing. In such cases the activated surface may be protected immediately after the surface treatment by a thin organic coating, namely the primer.

Primers generally consist of dilute solutions of the basic adhesive components which should also be used for the subsequent bonding. These solutions are normally applied to the substrates to be bonded by a rolling or dip-coating procedure and are cured at temperatures (in the case of primers based on chemically reacting bonding systems) below the temperature subsequently used to cure the adhesive. This procedure ensures both good adhesion of the layer of primer on the surface of the substrate to be bonded, as well as subsequent additional curing to form a joint polymer structure with the adhesive applied. Primers are also used to provide additional protection against the seepage of moisture into the joint and thus from the effects of creeping corrosion. Such a procedure is used in particular for bonding aluminum alloys in aircraft construction.

Examples of effective primers are aminoalkylalkoxy silanes (see Plueddemann et al. "Silane coupling agents", Plenum Press, New York [1982]). The most effective aminosilane adhesion promoters must not, however, be used in unmodified form as adhesion promoters incorporated into moisture-curable polyurethanes, as the amino groups react with isocyanate groups. For this reason, German Offenlegungsschrift No. 34 14 877 proposes the use of ketimines and aldimines of aminoalkylsilanes which can be added to polyurethane adhesives without impairing their storage stability.

European patent application EP-A No. 182,924 also proposes isocyanate group-containing silanes for use in acrylic resins.

The present invention relates to compounds of the general formula I

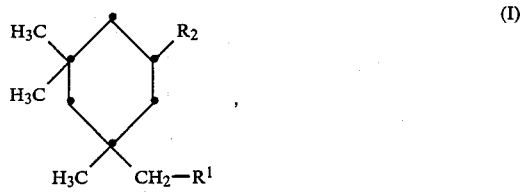

wherein one of the substituents $R^1$ or $R^2$ is $-N=C=O$ and the other is $-NHC(O)S(CH_2)_3Si(OR^3)_3$, wherein $R^3$ is $C_1$-$C_4$ alkyl or phenyl.

$R^3$ as a $C_1$-$C_4$ alkyl group may, for example, be methyl, ethyl, n-propyl, isopropyl, n-butyl, sec-butyl or tert-butyl.

Preferred compounds of formula I are those wherein $R^2$ is $-N=C=O$, and particularly preferred are compounds of formula I obtained as mixtures of isomers, wherein $R^1$ is $-N=C=O$ and those wherein $R^2$ is $-N=C=O$. The mixtures of isomers are formed during the synthesis of compounds of formula I from isophorone diisocyanate of formula II

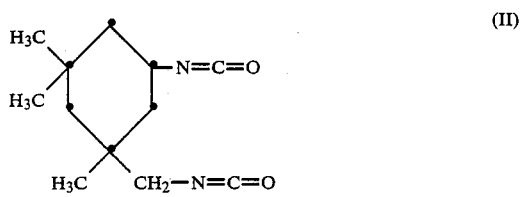

and a mercaptosilane of formula III

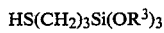

wherein R³ has the meaning given above. These mixtures are preferably used without separation of the isomers. If separation is desired, it may be effected by conventional methods of separating isomers.

The above described reaction is preferably carried out in the presence of a catalyst. Choice of a suitable catalyst makes it possible to control the addition reaction so that the attack of the mercaptosilane of formula III preferably occurs at the primary or, most preferably, at the secondary, —NCO-group. If, for example, 1,4-diazabicyclo[2.2.2]octane is used as catalyst, the primary —NCO-group proves to be more reactive, whereas the presence of dibutyltin dilaurate promotes reaction at the secondary —NCO-group, as is also the case when no catalyst is used. Concerning the preparation of compounds of formula I, reference is made for example to Ono et al., J. Pol.Sc., Pol.Lett. Ed.23, 509–515.

Preferred catalysts are those which are conventionally used in the preparation of moisture-curable polyurethanes.

The preferred ratio of compounds II:III in this reaction is 0.5 to 1.5:1 and, in particular, about 1:1.

A particular advantage of the compounds of formula I is the fact that they are suitable both for moisture-curable (single-component) and also for polyol-curable (two-component) polyurethane systems. In both systems they result in a distinct improvement in the adhesive properties on glass, metal and plastics such as glass fibre-reinforced plastics. For the user, the compounds of the invention are particularly advantageous as they may be employed as primers and as adhesion promoters incorporated into the polyurethane adhesive. This feature is particularly surprising, as the addition of monofunctional isocyanate would be expected to have a highly detrimental effect on the curing of polyurethanes. When used in amounts of up to 20% by weight, based on the prepolymer component, neither impairment of curing nor formation of bubbles was observed during curing. The non-adhesive polyurethane prepolymers and the compounds of formula I result in systems which are distinguished by excellent mechanical properties.

The compounds of formula I are easy to handle. They are liquid, of low viscosity and, moreover, have excellent storage stability.

If moisture-curable polyurethanes (single-component adhesives) are used as substrate, they contain polyfunctional isocyanates and/or polyurethane prepolymers as main component. Particularly suitable in this connection are aromatic and aliphatic, monocyclic and polycyclic, polyfunctional isocyanate compounds. Thus, for example, in a first embodiment of the invention, the aromatic isocyanate compound may be toluylene diisocyanate or diphenylmethane diisocyanate. Technical diphenylmethane diisocyanate containing higher functional diisocyanates and having an isocyanate group functionality greater than 2 is particularly suitable. A suitable diisocyanate is xylylene diisocyanate. In addition, a large number of aliphatic isocyanates having a functionality of 2 and more may be used. Examples are isophorone diisocyanate and dicyclohexylmethane diisocyanate as cycloaliphatic diisocyanates. Further examples are the aliphatic, straight-chain diisocyanates which are obtained by phosgenation of diamines, for example tetramethylene diisocyanate or hexamethylene diisocyanate.

In a preferred embodiment of the invention, polyurethane prepolymers are used in place of the polyfunctional isocyanate compounds. The term prepolymers is used in this context to refer to the adducts of an excess of polyfunctional isocyanates with polyfunctional alcohols, for example the reaction product of one of the above-mentioned aromatic or aliphatic diisocyanates with ethylene glycol, propylene glycol, glycerol, trimethylolpropane or pentaerythritol. Reaction products of diisocyanates with polyether polyols, e.g. polyether polyols of polyethylene oxide or on the basis of polypropylene oxide may also be used as prepolymers. Polyurethane prepolymers based on polyether polyols having molecular weights between 200 and 10,000, in particular between 500 and 3000 are preferred. A large number of such polyether polyols are known to the expert in polyurethane chemistry. They are available from numerous suppliers and are characterised by their molecular weight (number average) which may be calculated by end group analysis. Other polyether polyols which may be used are polyether polyols based on polytetrahydrofuran.

Instead of polyether polyols, it is also possible to use polyester polyols. Suitable polyester polyols are reaction products of polyfunctional acids with polyfunctional alcohols, for example polyesters derived from aliphatic and/or aromatic dicarboxylic acids and polyfunctional alcohols having a functionality of 2–4. Thus it is possible, on the one hand, to use polyesters derived from adipic acid, sebacic acid, phthalic acid, hydrophthalic acid and/or trimellitic acid and, on the other hand, ethylene glycol, propylene glycol, neopentyl glycol, hexane glycol, glycerol and/or trimethylolpropane. Particularly suitable polyester polyols are those having a molecular weight (number average) between 500 and 5000, in particular between 600 and 2000. Other suitable polyester polyols are the reaction products of caprolactone with alcohols having a functionality of from 2–4, such as the adduct of 1–5 moles of caprolactone with 1 mole of ethylene glycol, propylene glycol, glycerol and/or trimethylolpropane.

A further suitable class of polyfunctional alcohols is that of the polybutadienols. These are hydroxyl-terminated butadiene oligomers. Suitable products are those having molecular weights in the range of 200–4000, in particular 500–3000.

In the preparation of the polyurethane prepolymers, the ratio of OH groups of the alcohol components to isocyanate groups is important. This ratio is generally from 1:2 to 1:10. Polyurethane prepolymers of more or less low visocsity are obtained when using large excesses of isocyanate, whereas smaller excesses of isocyanate yield highly viscous preparations that can generally only be flat coated.

The polyurethane expert knows that the density of cross-linking, and hence the hardness and brittleness of polyurethanes, increases with the functionality of the isocyanate compounds or also that of the polyol. Reference is made here to the general technical literature, e.g. to the monograph by Saunders and Frisch "Polyurethanes, Chemistry and Technology", Volume XVI of the High Polymers series by Interscience Publishers New York-London, Part I (1962) and Part II (1964).

The expert knows from the same source, for example, that, in the case of polyol-curable two-component adhesives, he can use the same polyols as described above for the manufacture of the prepolymers. In this case it is only necessary to alter the ratio of OH groups of the alcohol components to isocyanate groups in favour of the alcohol component. If an excess of isocyanate groups is used at all, it should not exceed 2% of theory.

In two-component systems, the silane of formula 1 should preferably be in the isocyanate component.

The polyurethane formulations of the invention may, furthermore, contain various auxiliaries. For example they may contain fillers. Suitable fillers are inorganic compounds which do not react with isocyanates, e.g. chalk or ground lime, precipitated and/or pyrogenic silicic acids, zeolites, bentonites, ground minerals as well as other inorganic fillers known to the person skilled in the art, in particular ground fibres and the like. For some applications fillers are preferred which impart thixotropic properies to the compositions, such as swellable plastics, in particular PVC.

In addition to the cited compounds, the polyurethane compositions of the invention may contain other auxiliaries such as solvents. Suitable solvents are those which do not themselves react with isocyanate groups, e.g. halogenated hydrocarbons, esters, ketones, aromatic hydrocarbons, and the like. Plasticizers, flame retardants, retarders, colorants and ageing inhibitors conventionally used in polyurethane adhesives sealing compounds may be incorporated in the polyurethane compositions.

For some applications it is desirable to add foam stabilisers to the polyurethane compositions of the invention. These foam stabilisers may be silicone surfactants. These are block copolymers obtained from a polysiloxane block and one or more polyoxyethylene and/or polyoxypropylene blocks. The polyurethane compositions of the invention may also contain flame inhibiting and plasticizing additives. Commonly used additives of this kind are those containing phosphorus and/or halogen atoms, e.g. tricresyl phosphate, diphenylcresyl phosphate, tris(2-chloroethyl)phosphate, tris(2-chloropropyl)phosphate and tris(2,3-dibromopropyl)phosphate. In addition it is possible to use flame retardants, for example chlorinated paraffins, halophosphides, ammonium phosphate and resins containing halogens and phosphorus. Further additives which may be of advantage for certain applications are plasticizers. Suitable plasticizers may for example be phthalic acid esters or esters of long-chain dicarboxylic acids, for example sebacic acid or azelaic acid esters. Epoxy plasticizers, such as epoxidized fatty acid derivatives, may also be used.

Other possible additives are basic accelerators. These compounds should not be used if carboxylic acid anhydrides are used as accelerators. Basic accelerators are for example tertiary bases such as bis(N,N'-dimethylamino)diethylether, dimethylaminocyclohexane, N,N-dimethylbenzylamine, N-methylmorpholine as well as the reaction products of dialkyl-($\beta$-hydroxyethyl)amine with monoisocyanates and esterification products of dialkyl-($\beta$-hydroxyethyl)amine and dicarboxylic acids. Another important accelerator is 1,4-diaminobicyclo(2.2.2)octane. It is, moreover, possible to use non-basic compounds as accelerators, for example metal compounds such as iron pentacarbonyl, nickel tetracarbonyl, iron acetylacetonate as well as tin(II)-2-ethylhexanoate, dibutyltin dilaurate or molybdenum glycolate.

The adhesion promoters are usually added to the adhesives in amounts of 1–20% by weight, preferably 5–15% by weight, based on the isocyanate-terminated prepolymer in the case of single-component systems or based on the isocyanate component in the case of two-component systems.

When used as primer, the adhesion promoter of formula I may be applied direct to the substrate to form a film which can no longer be detached from the substrate after curing and storage. It is remarkable that the compounds according to the invention form films after as little as two to five minutes. It is, however, also possible and known to the expert to use the adhesion promoters together with a binder and, optionally, with a diluent. Particularly suitable binders are polymers having protected —OH groups, e.g. polyesters, such as polyacrylates or polyvinylbutyrates. Examples of suitable diluents are methyl ethyl ketone or methylene chloride.

EXAMPLE 1:

0.5 ml of dibutyltin dilaurate is added dropwise to a mixture of 222 g (1 mole) of isophorone diisocyanate and 196 g of 3-mercaptopropyl trimethoxysilane (1 mole). The mixture is stirred for 2 hours at 60° C. and then for 24 hours at 100° C., to give a liquid for which the following analytical data are obtained:

| Isocyanate content: 9.7% (calc. 10.0%) $n_D^{25} = 1.497$ ||||
|---|---|---|---|
| Elemental analysis | found: | theory: | for $C_{18}H_{34}N_2O_5SSi$ |
| % C | 51.67 | 51.64 | |
| % H | 8.28 | 8.19 | |
| % N | 6.74 | 6.69 | |
| % S | 7.71 | 7.66 | |
| IR (film on KBr): | | 3300 cm$^{-1}$, 2950 cm$^{-1}$, 2830 cm$^{-1}$, 2280 cm$^{-1}$, 1630 cm$^{-1}$, 1515 cm$^{-1}$, 1483 cm$^{-1}$, 1200 cm$^{-1}$, 1095 cm$^{-1}$, 850 cm$^{-1}$, | |
| $^1$H-NMR(100 MHz): | | 1 ppm(m), 1.75 ppm(m), 3 ppm(m), 3.6 ppm(s). | |

EXAMPLE 2:

(A) Prepolymer synthesis

A mixture of 177 g of dry polypropylene glycol having a molecular weight of 2000 (Desmophen ® 1900U), 0.9 g of trimethylol propane and 0.1 ml of dibutyltin dilaurate is added to methylene diphenyl diisocyanate (Isonate ® 125M) under nitrogen at 80° C. and the mixture is stirred for two hours at 80° C. An isocyanate-terminated prepolymer having an isocyanate content of 3.7% is obtained. (Prepolymer A).

(B) The bonding of steel to glass and adhesion to glass

The adhesion promoter is added to the prepolymer A and the moisture-curable single-component polyurethane is used to bond steel test pieces (17×2.5 cm) having an overlap of 1.25×2.5 cm and between which is sandwiched a glass slide (3.8×2.5 cm). In addition, a 0.3 cm layer of the adhesive is applied to a glass plate and, after curing for two weeks, stored in water for four weeks. The experiments in which the cured polyurethane could no longer be stripped manually from the glass after storage in water are designated with (+), whereas easy removal is indicated by (−).

| Silane of Ex. 1 (% based on prepolymer A) | Steel/glass shear strength (N/mm²) | Type of failure* | SMC/SMC** shear strength (N/mm²) | Adhesion to glass |
|---|---|---|---|---|
| — | 0.64 | A | 3.6 | — |
| 13 | 0.57 | M | 5.0 | + |
| 11 | 0.76 | M | 4.4 | + |
| 3 | 1.20 | C | 3.6 | + |

*A: adhesive failure, C: cohesive failure, M: glass breakage
**Glass fiber reinforced polyester

EXAMPLE 3:

A mixture of dry polypropylene glycol having a molecular weight of 2000 (DESMOPHEN® 1900U), 0.9 g of trimethylolpropane, 60 g of carbon black, 5 g of CAB-O-SIL® (pyrogenic silicic acid) and 0.2 ml of dibutyltin dilaurate is added to methylene diphenyl diisocyanate (ISONATE® 125M) under nitrogen at 80° C. The resulting mixture is stirred for two hours at 80° C. until an isocyanate content of 2.9% is obtained. After addition of 34 g of silane of Example 1, different specimens are bonded as described in Example 2.

| Substrate | Type of failure | Shear strength (N/mm²) |
|---|---|---|
| SMC/SMC | C | 8.2 |
| Steel/glass/steel | C | 0.9* |
| Aluminium/aluminium | C | 2.8 |

*Specimens were stored at room temperature for one week in water after curing for two weeks.

EXAMPLE 4:

A mixture of 177 g of dry polypropylene glycol MW 2000 (DESMOPHEN® 1900U), 0.9 ml of trimethylolpropane and 0.3 ml of dibutyltin dilaurate is added to 33.6 g of hexamethylene diisocyanate under nitrogen at 120° C. The mixture is stirred for two hours until an isocyanate content of 2.7% is obtained. Then 14 g of the adhesion promoter of Example 1 are added and the various substrates are bonded:

| Substrate | Shear strength (N/mm²) |
|---|---|
| SMC/SMC | 1.9 |
| Steel/glass/steel | 0.42 (glass breakage) |

EXAMPLE 5:

(Glass primer).

10 g of polyvinyl butyral (MOWITAL B70H from Hoechst) are dissolved in 200 g of methylene chloride (dried over neutral aluminum oxide) and to the solution are added 15 g of the adhesion promoter of Example 1. Using a brush or a drawing frame the solution can be applied to glass to form a film within one minute which, after curing at room temperature for three days, can no longer be detached on subsequent storage in water.

EXAMPLE 6:

(Adhesion to different substrates)

Within one hour at 70° C., 77.7 g of dry polypropylene glycol (MW 2000, DESMOPHEN® 1900U) are added to 21.9 g of methylene diphenyl diisocyanate which contains 0.04 ml of dibutyltin dilaurate. After addition of 0.39 g of trimethylolpropane, stirring is continued for a further hour at 70° C. An isocyanate-terminated polyurethane prepolymer having a 3.7% content of free isocyanate is obtained. To this moisture-curable prepolymer is added the adhesion promoter of Example 1 and the so modified adhesive is applied to different substrates. The batches are listed in the following table, where + indicates that it was not possible to detach the cured polyurethane layer manually from the substrate, which fact was taken as qualitative indication of adhesion promotion.

| Silane according to Ex. 1 (% relating to prepolymer) | ABS | PA | PC | PP | PVC | Steel | G |
|---|---|---|---|---|---|---|---|
| — | — | — | + | — | — | — | — |
| 5 | + | + | + | — | + | + | + |
| 15 | + | + | + | — | + | + | + |

ABS: acrylonitrile-butadiene-styrene
PA: polyamide
PC: polycarbonate
PP: polypropylene
PVC: polyvinylchloride
G: glass

EXAMPLE 7:

(2-Component-PUR adhesive)

(A) Polyol component 50 g of hydroxyl terminated polybutadiene (POLY BD® R45 HT) are mixed with 5 g of 2-ethyl-1,3-hexanediol, 43 g of filler (SILLITHIN® Z86) and 2 g of Cab-O-Sil® and dried for one hour under vacuum at 80° C.

(B) Bonding of polycarbonate and glass (2.00 mm joint).

Different mixtures consisting of polyol (A), a liquid 4,4'-diisocyanatodiphenylmethane (ISONATE® 143L) and an adhesion promoter (according to Example 1) were tested after curing for 30 minutes at 80° C.:

| Polyol (g) | Isocyanate (g) | Adhesion promoter (g) | Shear strength (N/mm²) | Elongation at break (mm) | Type of failure |
|---|---|---|---|---|---|
| 5 | 0.75 | — | 2.2 | 4.0 | AF |
| 5 | 0.85 | — | 2.2 | 3.7 | AF |
| 5 | 0.70 | 0.2 | 2.6 | 5.8 | C,MF |
| 5 | 0.70 | 0.3 | 2.8 | 6.8 | C,MF |

AF = adhesive failure
C = cohesive failure
MF = material failure

What is claimed is:

1. A two component adhesive consisting essentially of
   (I) a polyfunctional isocyanate compound or an isocyanate terminated polyurethane prepolymer and a compound of formula I

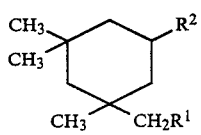

(I)

wherein one of the radicals $R^1$ or $R^2$ is $-N=C=O$ and the other is $-NHC(O)S(CH_2)_3Si(OR^3)_3$, wherein $R^3$ is $C_1$-$C_4$ alkyl or phenyl and
   (II) as a curing agent, a polyol with the proviso that the ratio of NCO groups to OH groups is less than or equal to 1.02.

* * * * *